(12) United States Patent
Magee

(10) Patent No.: US 9,358,042 B2
(45) Date of Patent: Jun. 7, 2016

(54) EXPANDABLE MEMBER FOR PERFORATION OCCLUSION

(71) Applicant: The Spectranetics Corporation, Colorado Springs, CO (US)

(72) Inventor: Matthew Miles Magee, Monument, CO (US)

(73) Assignee: The Spectranetics Corporation, Colorado Springs, CO (US)

(*) Notice: Subject to any disclaimer, the term of this patent is extended or adjusted under 35 U.S.C. 154(b) by 402 days.

(21) Appl. No.: 13/801,659

(22) Filed: Mar. 13, 2013

(65) Prior Publication Data
US 2014/0276402 A1  Sep. 18, 2014

(51) Int. Cl.
  *A61M 29/00* (2006.01)
  *A61M 25/10* (2013.01)
  *A61B 19/00* (2006.01)
  *A61B 17/34* (2006.01)
  (Continued)

(52) U.S. Cl.
  CPC ......... *A61B 17/3468* (2013.01); *A61B 17/1204* (2013.01); *A61B 17/12036* (2013.01); *A61B 17/12109* (2013.01); *A61B 17/12136* (2013.01); *A61M 25/10* (2013.01); *A61M 25/1002* (2013.01); *A61N 1/0587* (2013.01)

(58) Field of Classification Search
  CPC ............ A61M 25/10; A61M 25/1002; A61M 25/104; A61M 2025/1047; A61M 2025/1052; A61M 2025/1095; A61M 2025/1097; A61M 2025/105; A61M 2025/0183; A61N 2001/0578; A61N 2001/0587; A61N 1/056; A61N 1/0587; A61B 17/12036; A61B 17/12031; A61B 17/12022; A61B 17/1204; A61B 17/12109; A61B 17/12136; A61B 17/3468

USPC .......................................................... 606/129
See application file for complete search history.

(56) References Cited

U.S. PATENT DOCUMENTS 3,834,394 A    9/1974   Hunter et al.
4,413,989 A   11/1983   Schjeldahl et al.
              (Continued)

FOREIGN PATENT DOCUMENTS

EP    0760688 B1   11/2001
EP    0981387 B1   11/2003
         (Continued)

OTHER PUBLICATIONS

International Search Report and Written Opinion issued for PCT/US2014/019274 mailed Jun. 3, 2014, 14 pages.

*Primary Examiner* — Eric Rosen
*Assistant Examiner* — Christopher L Templeton
(74) *Attorney, Agent, or Firm* — Faegre Baker Daniels LLP

(57) ABSTRACT

Lead extraction is the removal of one or more leads from inside the heart utilizing a lead removal catheter having a tubular sheath that is placed in the blood vessel, either subclavian or femoral. The sheath of the lead removal catheter may accidentally tear or perforate the blood vessel as it is advanced over the lead toward the heart. Such an occurrence must be dealt with quickly to prevent harm to the patient or subject. An expandable member, such as a balloon, attached to the exterior of the sheath of a lead removal catheter can be deployed temporarily adjacent the perforation in the vessel wall. Inflation of the balloon not only stops (or substantially stops) the bleeding, but, upon inflation, the balloon may include one or more channels that allow blood to continue to flow through the channel(s) until the blood vessel perforation can be repaired.

5 Claims, 2 Drawing Sheets

(51) Int. Cl.
*A61B 17/12* (2006.01)
*A61N 1/05* (2006.01)

(56) References Cited

U.S. PATENT DOCUMENTS

| | | | |
|---|---|---|---|
| 4,545,390 A | 10/1985 | Leary | |
| 4,689,041 A | 8/1987 | Corday et al. | |
| 4,836,204 A * | 6/1989 | Landymore | A61B 17/0057 604/101.05 |
| 5,273,536 A | 12/1993 | Savas | |
| 5,304,121 A | 4/1994 | Sahatjian | |
| 5,338,298 A | 8/1994 | McIntyre | |
| 5,383,856 A | 1/1995 | Bersin | |
| 5,417,689 A | 5/1995 | Fine | |
| 5,439,445 A | 8/1995 | Kontos | |
| 5,447,497 A | 9/1995 | Sogard et al. | |
| 5,470,313 A | 11/1995 | Crocker et al. | |
| 5,496,311 A | 3/1996 | Abele et al. | |
| 5,540,679 A | 7/1996 | Fram et al. | |
| 5,599,306 A | 2/1997 | Klein et al. | |
| 5,759,170 A | 6/1998 | Peters | |
| 5,766,151 A | 6/1998 | Valley et al. | |
| 5,795,331 A * | 8/1998 | Cragg et al. | 604/103.01 |
| 5,800,393 A | 9/1998 | Sahota | |
| 5,820,595 A | 10/1998 | Parodi | |
| 5,823,996 A | 10/1998 | Sparks | |
| 5,843,116 A | 12/1998 | Crocker et al. | |
| 5,865,787 A | 2/1999 | Shapland et al. | |
| 5,885,244 A | 3/1999 | Leone et al. | |
| 5,985,307 A | 11/1999 | Hanson et al. | |
| 6,071,271 A | 6/2000 | Baker et al. | |
| 6,159,197 A * | 12/2000 | Heuser | 604/506 |
| 6,176,821 B1 | 1/2001 | Crocker et al. | |
| 6,221,043 B1 | 4/2001 | Fischell et al. | |
| 6,258,019 B1 | 7/2001 | Verin et al. | |
| 6,293,924 B1 | 9/2001 | Bagaoisan et al. | |
| 6,315,757 B1 | 11/2001 | Chee et al. | |
| 6,346,092 B1 | 2/2002 | Leschinsky | |
| 6,458,069 B1 | 10/2002 | Tam et al. | |
| 6,461,327 B1 | 10/2002 | Addis et al. | |
| 6,485,500 B1 | 11/2002 | Kokish et al. | |
| 6,491,663 B1 | 12/2002 | Lemelson | |
| 6,572,633 B1 | 6/2003 | Loffler et al. | |
| 6,579,847 B1 | 6/2003 | Unger | |
| 6,613,066 B1 | 9/2003 | Fukaya et al. | |
| 6,616,629 B1 | 9/2003 | Verin et al. | |
| 6,623,504 B2 | 9/2003 | Vrba et al. | |
| 6,626,861 B1 | 9/2003 | Hart et al. | |
| 6,629,952 B1 | 10/2003 | Chien et al. | |
| 6,645,167 B1 * | 11/2003 | Whalen, II | C08J 3/091 424/423 |
| 6,652,441 B2 | 11/2003 | Weinberger et al. | |
| 6,652,485 B1 | 11/2003 | Gaudoin et al. | |
| 6,656,153 B1 | 12/2003 | Sakai et al. | |
| 6,663,614 B1 | 12/2003 | Carter | |
| 6,679,900 B2 | 1/2004 | Kieturakis et al. | |
| 6,682,545 B1 | 1/2004 | Kester | |
| 6,699,170 B1 | 3/2004 | Crocker et al. | |
| 6,706,010 B1 | 3/2004 | Miki et al. | |
| 6,723,070 B1 | 4/2004 | Arai et al. | |
| 6,743,208 B1 | 6/2004 | Coyle | |
| 6,743,227 B2 | 6/2004 | Seraj et al. | |
| 6,875,209 B2 | 4/2005 | Zvuloni et al. | |
| 6,955,658 B2 | 10/2005 | Murray, III | |
| 6,960,186 B1 | 11/2005 | Fukaya et al. | |
| 7,137,395 B2 | 11/2006 | Fried et al. | |
| 7,169,140 B1 | 1/2007 | Kume | |
| 7,232,452 B2 | 6/2007 | Adams et al. | |
| 7,247,147 B2 | 7/2007 | Nishide et al. | |
| 7,306,575 B2 | 12/2007 | Barbut et al. | |
| 7,491,188 B2 | 2/2009 | Holman et al. | |
| 7,645,290 B2 | 1/2010 | Lucas | |
| 7,722,568 B2 | 5/2010 | Lenker et al. | |
| 7,727,228 B2 | 6/2010 | Abboud et al. | |
| 7,862,575 B2 | 1/2011 | Tal | |
| 7,862,577 B2 | 1/2011 | Gray et al. | |
| 7,909,794 B2 | 3/2011 | Briscoe et al. | |
| 7,931,663 B2 | 4/2011 | Farnan et al. | |
| 7,942,850 B2 | 5/2011 | Levit et al. | |
| 8,021,386 B2 | 9/2011 | Davidson et al. | |
| 8,177,779 B2 | 5/2012 | Joye et al. | |
| 8,221,342 B2 | 7/2012 | Mesallum | |
| 8,231,617 B2 | 7/2012 | Satake | |
| 8,235,941 B2 | 8/2012 | Hayman et al. | |
| 8,292,913 B2 | 10/2012 | Warnack et al. | |
| 8,323,307 B2 | 12/2012 | Hardert | |
| 8,348,890 B2 | 1/2013 | Gerrans et al. | |
| 8,372,034 B2 | 2/2013 | Levit et al. | |
| 8,382,787 B2 | 2/2013 | Burton et al. | |
| 8,414,611 B2 | 4/2013 | Chalekian | |
| 8,518,105 B2 | 8/2013 | Hossainy et al. | |
| 8,574,225 B2 | 11/2013 | Reynolds | |
| 8,667,838 B2 | 3/2014 | Hoem et al. | |
| 8,708,996 B2 | 4/2014 | Consigny et al. | |
| 8,740,961 B2 | 6/2014 | Fulton et al. | |
| 8,784,602 B2 | 7/2014 | Schaeffer et al. | |
| 8,801,662 B2 | 8/2014 | Doshi et al. | |
| 8,852,146 B2 | 10/2014 | Horn et al. | |
| 8,864,705 B2 | 10/2014 | Nishigishi | |
| 8,936,568 B2 | 1/2015 | Webler et al. | |
| 8,986,339 B2 | 3/2015 | Warnack et al. | |
| 2003/0004462 A1 * | 1/2003 | Halpin | 604/99.04 |
| 2003/0163154 A1 | 8/2003 | Miyata et al. | |
| 2003/0199914 A1 | 10/2003 | Diaz | |
| 2004/0006305 A1 | 1/2004 | Hebert et al. | |
| 2004/0122362 A1 | 6/2004 | Houser et al. | |
| 2004/0249243 A1 * | 12/2004 | Kleiner | A61B 1/00082 600/115 |
| 2004/0267196 A1 | 12/2004 | Miki et al. | |
| 2005/0015047 A1 | 1/2005 | Shah | |
| 2005/0033263 A1 | 2/2005 | Gottlieb et al. | |
| 2005/0075711 A1 | 4/2005 | Neary | |
| 2005/0209674 A1 | 9/2005 | Kutscher et al. | |
| 2006/0095065 A1 | 5/2006 | Tanimura et al. | |
| 2006/0173298 A1 | 8/2006 | Tucker | |
| 2006/0258981 A1 | 11/2006 | Eidenschink | |
| 2007/0203453 A1 | 8/2007 | Mori et al. | |
| 2009/0054922 A1 | 2/2009 | Broker | |
| 2009/0076447 A1 | 3/2009 | Casas et al. | |
| 2009/0105686 A1 | 4/2009 | Snow et al. | |
| 2009/0131785 A1 | 5/2009 | Lee et al. | |
| 2009/0192452 A1 | 7/2009 | Sasajima et al. | |
| 2009/0306700 A1 | 12/2009 | Miyata et al. | |
| 2010/0004623 A1 | 1/2010 | Hamilton et al. | |
| 2010/0185220 A1 | 7/2010 | Naghavi et al. | |
| 2010/0324648 A1 | 12/2010 | Scheller et al. | |
| 2011/0082465 A1 * | 4/2011 | Verma | A61B 17/12022 606/129 |
| 2011/0190727 A1 | 8/2011 | Edmunds et al. | |
| 2011/0190867 A1 | 8/2011 | Vonderwalde et al. | |
| 2012/0109177 A1 | 5/2012 | Ulmer | |
| 2012/0157987 A1 | 6/2012 | Steinke et al. | |
| 2012/0310210 A1 | 12/2012 | Campbell et al. | |
| 2013/0073025 A1 | 3/2013 | Kassab | |
| 2013/0090679 A1 | 4/2013 | Hoem et al. | |
| 2013/0165925 A1 | 6/2013 | Mathur et al. | |
| 2013/0211381 A1 | 8/2013 | Feld | |
| 2013/0310687 A1 | 11/2013 | Takizawa et al. | |
| 2014/0018732 A1 | 1/2014 | Bagaoisan et al. | |
| 2014/0094893 A1 | 4/2014 | Gerber | |
| 2014/0100646 A1 | 4/2014 | Hassan et al. | |
| 2014/0180248 A1 | 6/2014 | Salik | |
| 2014/0249475 A1 | 9/2014 | Pacetti | |
| 2014/0257181 A1 | 9/2014 | Speck | |
| 2014/0257266 A1 | 9/2014 | Kasprzyk et al. | |
| 2015/0080875 A1 | 3/2015 | Kasprzyk et al. | |
| 2015/0112256 A1 | 4/2015 | Byrne et al. | |

FOREIGN PATENT DOCUMENTS

| | | | |
|---|---|---|---|
| EP | 0853957 | B1 | 6/2004 |
| EP | 1129737 | B1 | 7/2005 |
| EP | 1051990 | B1 | 10/2008 |
| EP | 2002779 | A2 | 3/2009 |

(56) References Cited

FOREIGN PATENT DOCUMENTS

| | | |
|---|---|---|
| EP | 2331187 A2 | 9/2009 |
| EP | 2331196 A1 | 12/2009 |
| EP | 1879652 B1 | 6/2012 |
| EP | 1802368 B1 | 7/2013 |
| WO | 9402195 A1 | 2/1994 |
| WO | 9902202 A2 | 1/1999 |
| WO | 2004096339 A1 | 11/2004 |
| WO | 2010048729 A1 | 5/2010 |
| WO | 2010078875 A1 | 7/2010 |
| WO | 2012078612 A2 | 6/2012 |
| WO | 2014102611 A2 | 7/2014 |
| WO | 2014158687 A1 | 10/2014 |

\* cited by examiner

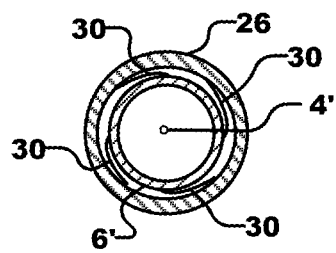
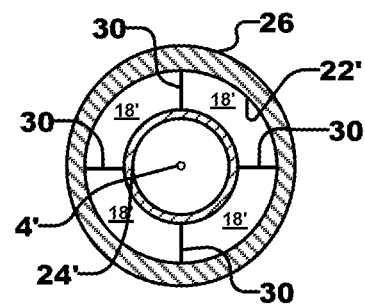
FIG. 4A　　　　FIG. 4B
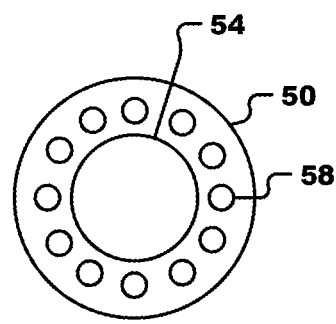
FIG. 5
PRIOR ART

EXPANDABLE MEMBER FOR PERFORATION OCCLUSION

FIELD

This disclosure relates generally to lead removal catheters and particularly to a lead removal catheter having an expandable member, such as a balloon, attached to thereto. The expandable member may be inflated within a patient's vascular system. Upon being inflated, the balloon creates a passageway between its interior and the sheath's exterior, thereby allowing blood to flow through the passageway.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached to the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including but not limited to, infections, lead age, and lead malfunction.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. An example of such a lead locking device is described and illustrated in U.S. Pat. No. 6,167,315 to Coe et al., which is incorporated herein by reference in its entirety for all that it teaches and for all purposes.

A mechanical device to extract leads includes a flexible tube called a sheath that passes over the lead and/or the surrounding tissue. The sheath typically may include a cutting blade, such that upon advancement, the cutting blade and sheath cooperate to separate the scar tissue from other scar tissue including the scar tissue surrounding the lead. In some cases, the cutting blade and sheath may also separate the tissue itself from the lead. Once the lead is separated from the surrounding tissue and/or the surrounding tissue is separated from the remaining scar tissue, the lead may be inserted into a hollow lumen of the sheath for removal and/or be removed from the patient's vasculature using some other mechanical devices, such as the mechanical traction device previously described in United States Patent Publication No. 2008/0154293 to Taylor, which is hereby incorporated herein by reference in its entirety for all that it teaches and for all purposes. Examples of a such devices and methods used to extract leads is described and illustrated in U.S. Pat. No. 5,651,781 to Grace, which is incorporated herein by reference in its entirety for all that it teaches and for all purposes.

Examples of a laser catheter assembly or laser sheaths that may be used for removing a surgically implanted lead is a coronary laser atherectomy catheter by the Spectranetics Corporation under the trade names SLSII™ and GlideLight™. FIG. 5 depicts the distal end of a flexible catheter 50 comprising multiple fiber optic laser emitters 58 surrounding a lumen 54. As the fiber optic laser emitters 58 cut the tissue surrounding the lead, the sheath slides over the lead and surrounding tissue, which enter the lumen.

Lead extraction is generally a very safe procedure. However, as with any invasive procedure, there are potential risks. For example, while using any of the tools discussed above to remove a lead, the tool may accidentally pierce, cut, or perforate the vein or artery through which the tool is traveling, thereby allowing blood to escape the patient's vascular system. The rate at which blood escapes, may be high if the accidental opening is created close to the patient's heart. Accordingly, a clinician must address the situation quickly to mitigate the amount of blood that escapes from the patient, thereby minimizing potential long-term harm to the patient.

SUMMARY

These and other needs are addressed by the various aspects, embodiments, and configurations of the present disclosure. The disclosure is generally directed to the use of a (typically radially or peripherally) expandable member, such as a balloon, attached to or otherwise engaged with the exterior of the sheath of a lead removal catheter or other type of catheter. The expandable member is positioned adjacent the vascular opening that is accidentally created by the lead removal catheter. Once positioned at the opening, the expandable member can be inflated, which will permit the exterior of the expandable member to press against or otherwise contact the opening and stop, or at least substantially minimize the bleeding. Upon expansion (e.g., inflation), a passageway is created through the interior of the expandable member, thereby allowing blood to flow from one side of the expandable member to the other and through the patient's vasculature system until the opening can be repaired. Typically, a clinician or surgeon will institute a separate procedure to surgically repair the site.

A method, according to this disclosure, can occlude an opening in a patient's vascular system by the steps of:

(a) advancing a sheath in a blood vessel until an expandable member engaged with the sheath is positioned at least substantially adjacent an opening in the blood vessel; and (b) expanding the expandable member, thereby at least substantially occluding the opening.

A device, according to this disclosure, can include:

(a) a catheter sheath having an outer surface; and (b) an expandable member attached to the sheath, the expandable member comprising an interior surface and an exterior surface, wherein the expandable member is capable of being expanded and, upon expansion, a channel is formed between the interior surface of the expandable member and the outer surface of the sheath.

A radially expandable member, according to this disclosure, can include:

(a) a radially expandable member comprising an annulus for receiving a sheath of a catheter;

(b) at least two flexible connecting members for connecting the radially expandable member to the sheath; and (c) at least two channels bound by an inner surface of the expandable member, an outer surface of the sheath, and the two or more flexible connecting members.

Blood can continue to flow through the blood vessel, by means of the channel, until the opening (e.g., perforation) can be repaired.

The expandable member can be an inflatable and deflatable balloon.

The cross section of the channel can be at least substantially eccentrically shaped.

The expandable member, when expanded, can be at least substantially cylindrical, and the sheath can be positioned in an annulus of the expandable member.

The expandable member can include and/or release a coagulant to facilitate blood clotting in the opening of the blood vessel.

In one procedure, as the sheath of a lead removal catheter is advanced over a lead, and the blood vessel is accidentally perforated by the tip of the sheath, the perforation can be detected with a fluoroscopic device, through monitoring blood pressure, or any other suitable method or means. Once detected, the sheath is advanced until the balloon is positioned over the perforation location, aided by fluoroscopy and markers collocated with the expandable member. The expandable member is then expanded, occluding the perforation. The channel or channels formed within the expandable member, depending upon the design and structure of the expandable member, can allow blood to flow through the channel or channels in the blood vessel until a surgeon can repair the damaged area.

The present disclosure can provide benefits relative to conventional lead removal procedures. Currently, when an accidental perforation is created in a patient's vascular system during a lead removal procedure, there are no methods to quickly stop the bleeding and provide time for a surgeon to go in and repair the vein perforation. Since the balloon is located proximal to the tip of the sheath, it is in a ready position to be inflated to quickly stop the bleeding, continue to allow blood to flow through the vascular system, and provide the surgeon time to prepare for and perform a repair procedure. Allowing blood to keep flowing through the subject's vascular system while simultaneously stopping the bleeding, reduces the likelihood of potentially further harm to the subject through blocked blood flow.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xm, Y1-Yn, and Z1-Zo, the phrase is intended to refer to a single element selected from X, Y, and Z, a combination of elements selected from the same class (e.g., X1 and X2) as well as a combination of elements selected from two or more classes (e.g., Y1 and Z3).

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

A "lead" is a conductive structure, typically an electrically insulated coiled wire. The electrically conductive material can be any conductive material, with metals and intermetallic alloys common. The outer sheath of insulative material is biocompatible and biostable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

"Eccentric" generally means a non-circular form. For example, when one member is located within another member and the inner member is not located within the geometric center of the outer member, the inner member is considered to be eccentric. For the purposes of this disclosure an "eccentric passageway," "eccentrically shaped passageway," "eccentrically shaped lumen" or other variations, as used herein, shall mean a passageway, particularly a lumen within a sheath or catheter, having a cross sectional opening that is non-circular.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof, shall include all those described in the summary of the invention, brief description of the drawings, detailed description, abstract, and the claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure, but to present selected concepts of the disclosure in a simplified form as an introduction to the more detailed description presented below. As will be appreciated, other aspects, embodiments, and configurations of the disclosure are possible, utilizing alone or in combination, one or more of the features set forth above or described in detail below.

BRIEF DESCRIPTION OF THE DRAWINGS

FIG. 4A shows a cross section view of another embodiment of a doughnut-shaped balloon in a deflated position.

FIG. 4B shows a cross section view of the embodiment of the doughnut-shaped balloon of FIG. 4A in an inflated position.

FIG. 5 shows the cross section of the distal end of a known prior art laser catheter.

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used, and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
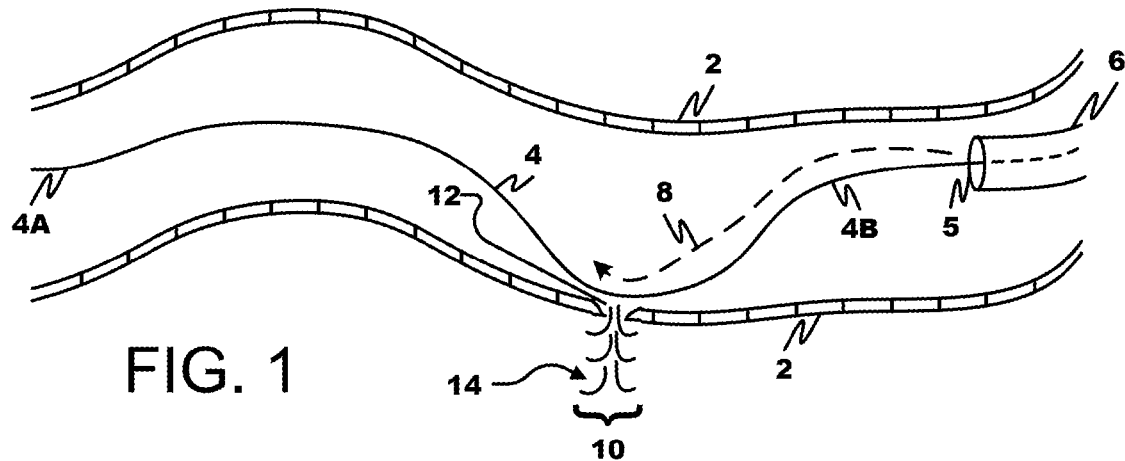
FIG. 1 shows a partial cross section view of a vein with an advancing sheath of a lead removal catheter that accidentally perforates the wall of the vessel.

FIG. 1 shows a partial cross-sectional view of a vein or other blood vessel with an advancing sheath of a lead removal catheter that accidentally perforates the wall of the vessel. Referring now to FIG. 1, blood vessel 2 terminates at the heart of a patient. Lead 4 lies within the blood vessel 2. Distal end 4A is connected to a surgically implanted device, such as a pacemaker or defibrillator proximal to the patient's heart. Sheath 6 of a lead removal catheter, having been threaded over lead 4, travels along lead 4 from the proximal end 4B of lead 4 in the direction indicated by dashed arrow 8. Lead 4 lies very close to a wall of blood vessel 2 at location 10. In such a situation, as sheath 6 is advanced along lead 4, the tip or cutting instrument of sheath 6 may accidently create a perforation 12 in the wall of blood vessel 2, thereby causing bleeding 14. Factors contributing to the occurrence of the perforation 12 may include: the sharpness of the bend in lead 4; the structural integrity of the wall of vein 2 at location 10; sharp bends in vein 2; the speed or force applied to the lead removal catheter in advancing sheath 6; and/or various combinations of these and other factors known to one skilled in the art.

Figure 2:
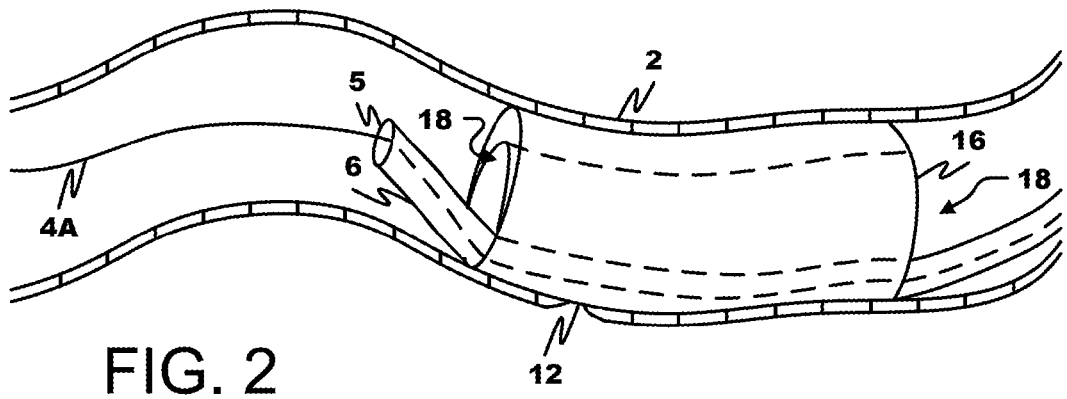
FIG. 2 shows a partial cross section view of the vein of FIG. 1 with the vein perforation occluded by an embodiment of a doughnut-shaped balloon.

FIG. 2 shows a partial cross-sectional view of the blood vessel of FIG. 1 with the perforation at least substantially occluded by an embodiment of an expandable member, such as a balloon. Referring now to FIG. 2, once perforation 12 has been detected with a fluoroscopic device, through monitoring blood pressure, or any other suitable method or means, sheath 6 is advanced farther along lead 4 until expandable member 16, which is attached to a portion of the circumference of sheath 6 and located proximally to distal tip 5 of the sheath 6, is positioned adjacent perforation 12. The position of expandable member 16 can be determined using known techniques, such as one or more radiopaque or other type of imaging markers (not shown) positioned in proximity to or adjacent to expandable member 16. An imaging technique, such as x-ray imaging, magnetic resonance imaging, or ultrasonic imaging, can visually depict relative positions of perforation 12 and expandable member 16. Expandable member 16 is then expanded (e.g., inflated), thereby at least substantially occluding perforation 12 and thus stopping bleeding 14. As will be appreciated, expandable member 16 can include a medication, such as a coagulant (such as NovoSeven™), on an outer surface of the expandable member and/or in an inner volume of the expandable member and released upon member expansion through one or more perforations in the expandable member, thereby potentially accelerating blood clotting. At the same time, blood within blood vessel 2 may flow from one side of expandable member 16 to the other side, thus continuing to flow through blood vessel 2 via a channel 18 (or annulus) formed by the expansion of expandable member 16. As a result, the patient is stabilized, giving the physician time to prep the patient for the procedure to be implemented to permanently repair perforation 12.

Figure 3A:
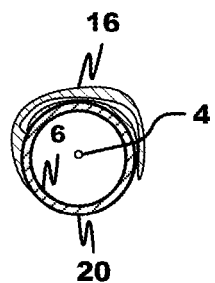
FIG. 3A shows a cross section view of an embodiment of a doughnut-shaped balloon in a deflated position.

FIG. 3A shows a cross-sectional view of an embodiment of an expandable member 16 in a deflated position. Referring to FIG. 3A, expandable member 16 is shown in cross section in a deflated or unexpanded position. Expandable member 16 is attached to or otherwise engages sheath 6 at adhesion area 20 which runs along a substantial length of expandable member 16 and catheter sheath 6 through methods known by those skilled in the art. The bulk of expandable member 16 is folded on itself and wrapped around sheath 6 as shown.

Figure 3B:
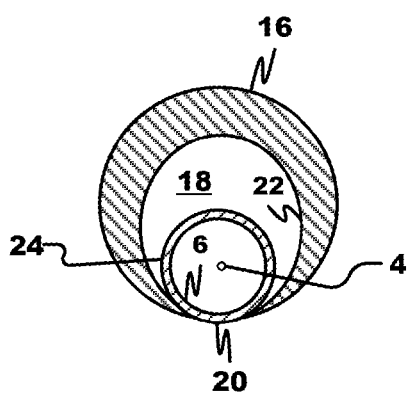
FIG. 3B shows a cross section view of the embodiment of a doughnut-shaped balloon of FIG. 3A in an inflated position.

FIG. 3B shows a cross-sectional view of the embodiment of expandable member 16 of FIG. 3A in an inflated or expanded position. Referring to FIG. 3B, expandable member 16 is shown in cross section in an expanded position. In the expanded position, channel 18 is formed by inner surface 22 of expandable member 16 and outer surface 24 of sheath 6. As illustrated in this figure, the cross section of channel 18 has an eccentric shape. The eccentric shape of the cross section of channel 18 is a result of gluing, welding, bonding, or through any other suitable attachment means, a linear length of expandable member 16 to sheath 6. Thus, blood will continue to flow in blood vessel 2 via channel 18 that is formed after expansion of expandable member 16.

FIG. 4A shows a cross-sectional view of another embodiment of an expandable member, configured as a doughnut-shaped balloon, in a deflated position. Referring to FIG. 4A, expandable member 26 is shown in cross section in a deflated position. Expandable member 26 is attached to sheath 6' via four flexible connecting members 30. Less than four flexible connecting members 30, such as two or three, may also be used, as well as more than four flexible connecting members 30, such as five or more.

FIG. 4B shows a cross-sectional view of the embodiment of the expandable member of FIG. 4A in an inflated position. Referring now to FIG. 4B, expandable member 26 is shown in cross section in an inflated position. In the inflated position, four channels 18' are formed by the inner surface 22' of expandable member 26, the surfaces of four flexible connecting members 30, and outer surface 24' of the catheter sheath 6'. With two flexible connecting members 30, two channels 18' would be formed. With three flexible connecting members 30, three channels 18' would be formed. With each additional flexible connecting member 30 added, one additional channel 18' will be formed. Thus, blood will continue to flow in blood vessel 2 via one or more channels 18' that are formed after inflation of expandable member 26. Substituting expandable member 26 for expandable member 16 shown in FIGS. 2, 3A, and 3B, expandable member 26 may be used in the same fashion as expandable member 16 described above. Many other configurations and methods for securing an expandable member to the catheter sheath are possible and fall within the scope of this disclosure, though not shown, but well known by one skilled in the art. These include, for example, (1) an expandable braided structure with a sleeve around the braided structure; and (2) memory shaped metal housed within a sleeve that once the sleeve is refracted the memory shaped metal can expand and contact the vessel walls.

A number of variations and modifications of the disclosure can be used. It would be possible to provide for some features of the disclosure without providing others.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and\or reducing cost of implementation.

The foregoing discussion of the disclosure has been presented for purposes of illustration and description. The foregoing is not intended to limit the disclosure to the form or forms disclosed herein. For example, in the foregoing Detailed Description, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspect, embodiment, and configuration. Thus, the following claims are hereby incorporated into this Detailed Description, with each claim standing on its own as a separate preferred embodiment of the disclosure.

Moreover, though the description of the disclosure has included descriptions of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for occluding an opening in a patient's vascular system, the method comprising:
   (a) advancing a sheath comprising a lumen and an expandable member in a blood vessel until the expandable member is positioned at least substantially adjacent an opening in the blood vessel; and
   (b) expanding the expandable member, thereby at least substantially occluding the opening in the blood vessel;
   (c) positioning the sheath over a lead, wherein the lead is disposed within the lumen, prior to the advancing step (a); and
   (d) advancing the sheath over the lead in the blood vessel, wherein the lead is disposed within the lumen;
   wherein the steps (a) through (d) are performed in the course of a lead removal procedure, wherein the lead is or was attached to one of a pacemaker and defibrillator.

2. The method of claim 1, wherein the expandable member is an inflatable balloon.

3. The method of claim 1, further comprising:
   forming a channel bounded by an inner surface of the expandable member and an outer surface of the sheath such that blood may flow from a first side to a second side of the expandable member.

4. The method of claim 1, wherein the opening in the blood vessel is a perforation and wherein the step (a) further comprises the step of:
   using fluoroscopy to detect the perforation.

5. The method of claim 1, wherein the expandable member comprises and/or releases a coagulant to facilitate blood clotting in the opening in the blood vessel.

* * * * *